US011238976B2

(12) United States Patent
Fuchigami

(10) Patent No.: US 11,238,976 B2
(45) Date of Patent: Feb. 1, 2022

(54) INTERPRETATION SUPPORT APPARATUS AND NON-TRANSITORY COMPUTER READABLE MEDIUM

(71) Applicant: FUJIFILM Corporation, Tokyo (JP)

(72) Inventor: Takuya Fuchigami, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 252 days.

(21) Appl. No.: 16/366,732

(22) Filed: Mar. 27, 2019

(65) Prior Publication Data

US 2019/0304594 A1 Oct. 3, 2019

(30) Foreign Application Priority Data

Mar. 28, 2018 (JP) .............................. JP2018-061540

(51) Int. Cl.
*G16H 30/40* (2018.01)
*G06T 7/00* (2017.01)
(Continued)

(52) U.S. Cl.
CPC ............... *G16H 30/40* (2018.01); *A61B 6/48* (2013.01); *A61B 6/5211* (2013.01); *G16H 50/20* (2018.01); *A61B 6/03* (2013.01); *G06T 7/0012* (2013.01)

(58) Field of Classification Search
CPC .......... G16H 30/40; G16H 50/20; A61B 6/48; A61B 6/5211; A61B 6/03; G06T 7/0012
See application file for complete search history.

(56) References Cited

U.S. PATENT DOCUMENTS 6,266,453 B1 7/2001 Hibbard et al.
6,993,167 B1* 1/2006 Skladnev ............. A61B 5/0059
382/128
(Continued)

FOREIGN PATENT DOCUMENTS

JP   2003-529406 A   10/2003
JP   2004-180932 A   7/2004
(Continued)

OTHER PUBLICATIONS

Japanese Office Action, dated Dec. 22, 2020 for corresponding Japanese Application No. 2018-061540, with an English translation.
(Continued)

*Primary Examiner* — Shefali D Goradia
(74) *Attorney, Agent, or Firm* — Birch, Stewart, Kolasch & Birch, LLP

(57) ABSTRACT

A support program is a program for supporting creation of an interpretation report including a medical image obtained by examining a patient and a region of interest to focus on in the medical image. The support program causes a computer to function as: a reading unit that reads a plurality of interpretation reports created by a plurality of examinations on the same part of the same patient; a difference detection unit that sets one of the plurality of interpretation reports as a detection target interpretation report and sets the others as comparison target interpretation reports, compares regions of interest of the detection target interpretation report and the comparison target interpretation reports, and detects a region of interest, which is present in the comparison target interpretation reports but is not present in the detection target interpretation report, as a difference region; and a notification screen distribution unit that, in a case where the difference region is detected, notifies that the difference region has been detected.

10 Claims, 10 Drawing Sheets

(51) Int. Cl.
    *G16H 50/20*     (2018.01)
    *A61B 6/00*     (2006.01)
    *A61B 6/03*     (2006.01)

(56)     References Cited

U.S. PATENT DOCUMENTS

| | | | |
|---|---|---|---|
| 10,541,048 B2 * | 1/2020 | Zhang | G16H 10/60 |
| 2005/0107690 A1 * | 5/2005 | Soejima | G16H 30/20 |
| | | | 600/425 |
| 2006/0050943 A1 | 3/2006 | Ozaki et al. | |
| 2007/0083396 A1 | 4/2007 | Kanada et al. | |
| 2010/0256459 A1 * | 10/2010 | Miyasa | G16H 50/20 |
| | | | 600/300 |
| 2012/0183191 A1 | 7/2012 | Nakamura | |
| 2015/0072371 A1 | 3/2015 | Marugame | |
| 2016/0203263 A1 * | 7/2016 | Maier | G06T 7/0016 |
| | | | 705/2 |
| 2017/0243348 A1 * | 8/2017 | Sakamoto | A61B 6/468 |

FOREIGN PATENT DOCUMENTS

| | | |
|---|---|---|
| JP | 2005-148990 A | 6/2005 |
| JP | 2007-122679 A | 5/2007 |
| JP | 2011-92682 A | 5/2011 |
| JP | 2013-39230 A | 2/2013 |
| JP | 5958534 B2 | 8/2016 |
| WO | WO 2011/040473 A1 | 4/2011 |

OTHER PUBLICATIONS

Japanese Office Action, dated May 18, 2021, for corresponding Japanese Application No. 2018-061540, with an English translation.

* cited by examiner

FIG. 9

TERM CORRESPONDENCE TABLE (92)

BRAIN

| BLOOD VESSEL DOMINATING REGION | BRAIN LOBE |
|---|---|
| ANTERIOR CEREBRAL ARTERY REGION (ACA) | FRONTAL LOBE OR PARIETAL LOBE |
| MIDDLE CEREBRAL ARTERY REGION (MCA) | TEMPORAL LOBE OR FRONTAL LOBE OR PARIETAL LOBE |
| POSTERIOR CEREBRAL ARTERY REGION (PCA) | OCCIPITAL LOBE OR BRAINSTEM |
| ⋮ | ⋮ |

| BRAIN LOBE | AREA | BRODMANN BRAIN MAP |
|---|---|---|
| FRONTAL LOBE | MOTOR AREA (PRIMARY MOTOR AREA) | BA4 |
| | MOTOR ASSOCIATION AREA (PREMOTOR AREA) | BA6 |
| | PREFRONTAL AREA (FRONTAL ASSOCIATION AREA) | BA9-11 |
| | FRONTAL EYE AREA | BA8 |
| ⋮ | ⋮ | ⋮ |

DISEASE STATE

| DISEASE STATE A | DISEASE STATE A' OR DISEASE STATE A" |
|---|---|
| DISEASE STATE B | DISEASE STATE B' |
| ⋮ | ⋮ |

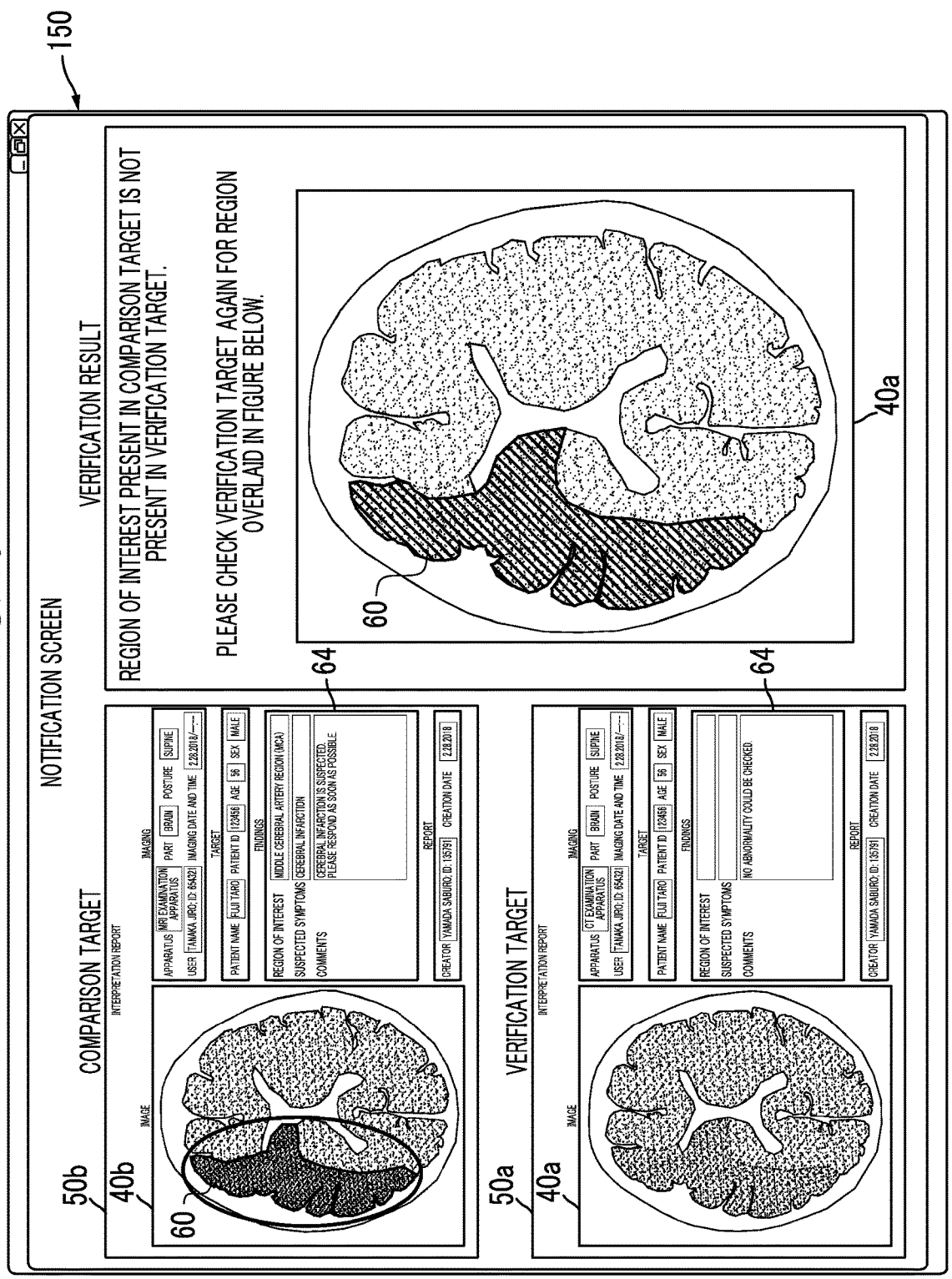

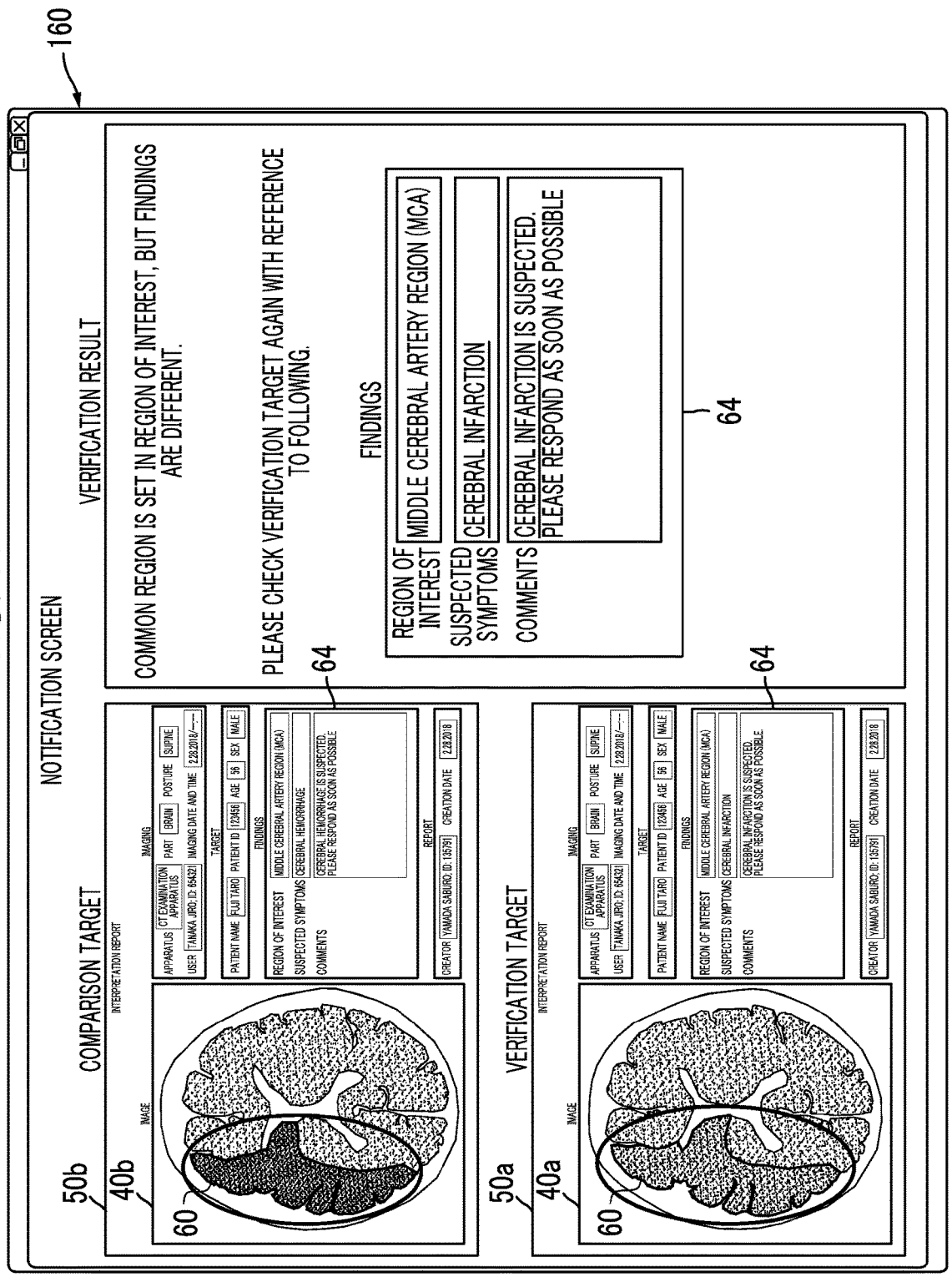

INTERPRETATION SUPPORT APPARATUS AND NON-TRANSITORY COMPUTER READABLE MEDIUM

CROSS-REFERENCE TO RELATED APPLICATIONS

This application claims priority under 35 U.S.C § 119(a) to Japanese Patent Application No. 2018-061540 filed on 28 Mar. 2018. The above application is hereby expressly incorporated by reference, in its entirety, into the present application.

BACKGROUND OF THE INVENTION

1. Field of the Invention

The present invention relates to an interpretation support apparatus and a non-transitory computer readable medium.

2. Description of the Related Art

In medical facilities, a radiologist interprets a medical image obtained by examining a patient and creates an interpretation report, and a treatment department doctor or a clinician determines a treatment policy based on the created interpretation report and performs actual treatment, which are widely performed acts. The interpretation report includes not only a medical image but also various kinds of information, such as a region of interest to focus on in the medical image and findings on the region of interest.

JP2004-180932A (corresponding to US2006/050943A1) and JP5958534B (corresponding to US2015/072371A1) disclose techniques for setting a region of interest for a medical image acquired by the current examination or creating findings on a region of interest with reference to information such as medical images, regions of interest, and findings stored in a database (hereinafter, abbreviated as a DB), that is, a technique for mechanically creating an interpretation report.

SUMMARY OF THE INVENTION

However, the method of mechanically creating an interpretation report as in JP2004-180932A and JP5958534B described above has low reliability, which is far from the reliability of the interpretation report created by the radiologist. As described above, the reliability of the interpretation report created by the radiologist is higher than the reliability of the mechanically created interpretation report. However, since the contents of the interpretation report are also a serious matter that may be relevant to the life of the patient, further improvement of the interpretation technique is required.

The invention has been made in view of the above background, and it is an object of the invention to provide an interpretation support apparatus and a non-transitory computer readable medium capable of contributing to the improvement of the interpretation technique.

In order to solve the aforementioned problem, the interpretation support apparatus of the invention is an interpretation support apparatus that supports creation of an interpretation report including a medical image obtained by examining a patient, a region of interest to focus on in the medical image, and findings on the region of interest. The interpretation support apparatus comprises: a reading unit that reads a plurality of interpretation reports created by a plurality of examinations on the same part of the same patient; a detection unit that sets one of the plurality of interpretation reports as a detection target interpretation report and sets the others as comparison target interpretation reports to be used for comparison with the detection target interpretation report, compares regions of interest of the detection target interpretation report and the comparison target interpretation reports, and detects a region of interest, which is present in the comparison target interpretation reports but is not present in the detection target interpretation report, as a difference region; and a notification unit that, in a case where the difference region is detected by the detection unit, notifies that the difference region has been detected.

In a case where the difference region is not present, for a common region of interest that is a region of interest common to both the detection target interpretation report and the comparison target interpretation reports, the detection unit may compare findings of the detection target interpretation report and findings of the comparison target interpretation reports regarding the common region of interest with each other and detect, as difference findings, findings not matching the findings of the comparison target interpretation reports in the findings of the detection target interpretation report. In a case where the difference findings are detected by the detection unit, the notification unit may notify that the difference findings have been detected.

The interpretation support apparatus of the invention may further comprise a storage unit that stores a correspondence table in which terms having the same meaning are associated with each other for terms used in the findings. The detection unit may detect the difference findings by accessing the storage unit to refer to the correspondence table.

In the correspondence table, a plurality of terms indicating each part may be associated with each other for each part of the patient.

The interpretation support apparatus of the invention may further comprise: an image deforming unit that deforms a comparison target medical image, which is a medical image of the comparison target interpretation report, such that a position of each portion matches a position of each portion of a detection target medical image, which is a medical image of the detection target interpretation report; and a display control unit that performs overlay display for displaying a region of interest of a deformed comparison target medical image, which is deformed by the image deforming unit, on a display unit so as to overlap the detection target medical image.

The display control unit may perform the overlay display for the difference region.

The detection target interpretation report and the comparison target interpretation report may be created based on examinations using the same examination apparatus.

The detection target interpretation report and the comparison target interpretation report may be created based on examinations using different examination apparatuses.

One of the detection target interpretation report or the comparison target interpretation report may be created based on an examination using a magnetic resonance imaging (MRI) examination apparatus, and the other one of the detection target interpretation report and the comparison target interpretation report may be created based on an examination using a computed tomography (CT) examination apparatus.

The examination may be a head examination, the detection target interpretation report may be created based on an examination using a computed tomography (CT) examination apparatus, and the comparison target interpretation report may be created based on an examination using a magnetic resonance imaging (MRI) examination apparatus.

A non-transitory computer readable medium of the invention is for storing a computer-executable program for supporting creation of an interpretation report including a medical image obtained by examining a patient, a region of interest to focus on in the medical image, and findings on the region of interest. The computer-executable program causes the computer to execute: a reading function of reading a plurality of interpretation reports created by a plurality of examinations on the same part of the same patient; a detection function of setting one of the plurality of interpretation reports as a detection target interpretation report and sets the others as comparison target interpretation reports to be used for comparison with the detection target interpretation report, compares regions of interest of the detection target interpretation report and the comparison target interpretation reports, and detects a region of interest, which is present in the comparison target interpretation reports but is not present in the detection target interpretation report, as a difference region; and a notification function of notifying that the difference region has been detected, in a case where the difference region is detected by the detection function.

According to the invention, it is possible to contribute to the improvement of the interpretation technique by detecting a region of interest (difference region), which is present in the comparison target interpretation report but is not present in the detection target interpretation report, and providing notification of the fact.

BRIEF DESCRIPTION OF THE DRAWINGS

FIG. 9 is an explanatory diagram of a term correspondence table.
FIG. 10 is an explanatory diagram of a notification screen.
FIG. 11 is an explanatory diagram of a notification screen.

DESCRIPTION OF THE PREFERRED EMBODIMENTS

Figure 1:
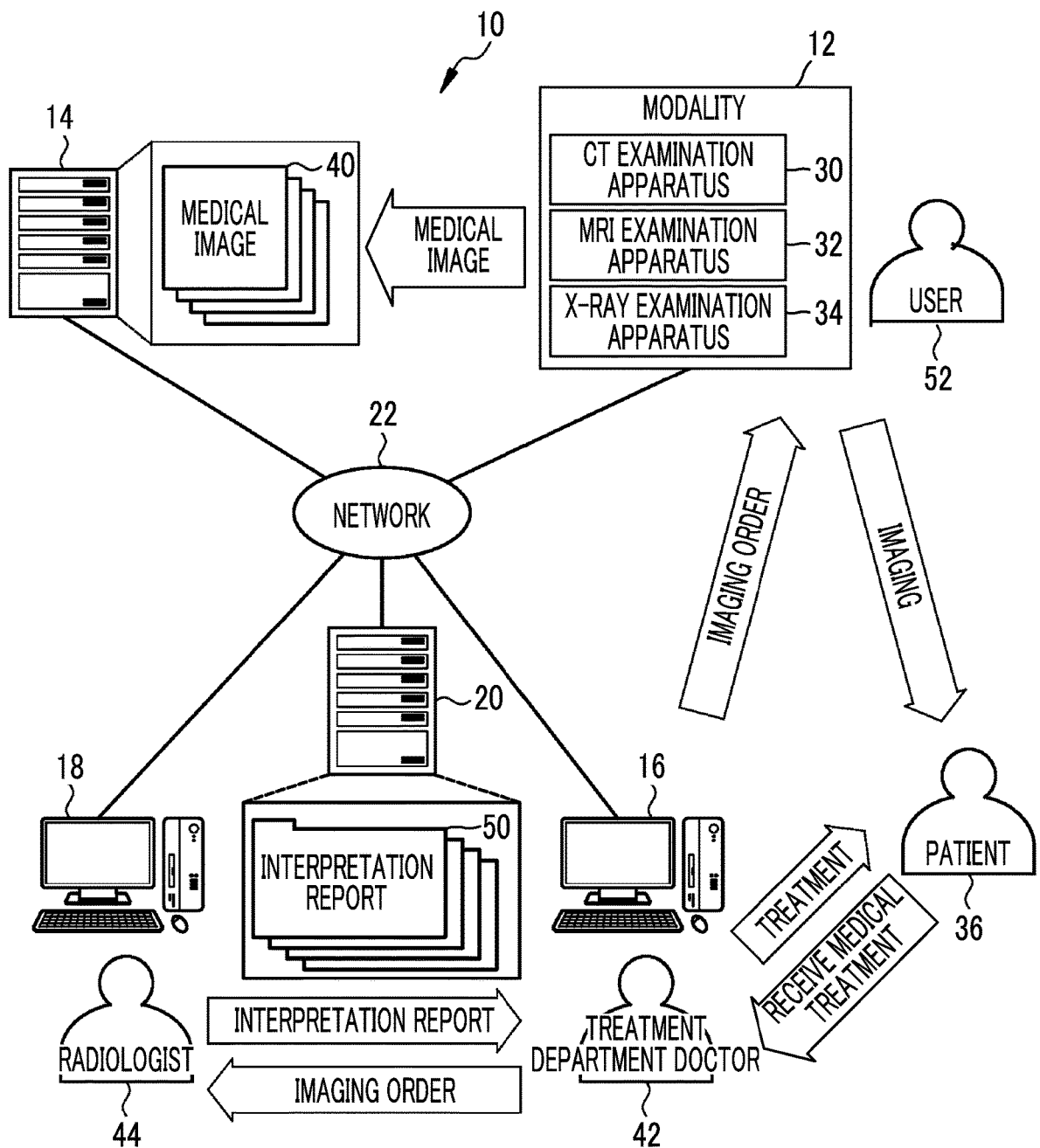
FIG. 1 is a schematic diagram of a medical information system.

In FIG. 1, a medical information system 10 is constructed in a medical facility, such as a hospital, and comprises a modality 12, a medical image DB server 14, a clinical terminal 16, an interpretation terminal 18, and an interpretation DB server 20 (interpretation support apparatus). These are connected to each other through a network 22, such as a local area network (LAN) constructed in the medical facility.

The modality 12 is an examination apparatus that acquires a medical image 40 by imaging a patient 36, such as a computed tomography (CT) examination apparatus 30, a magnetic resonance imaging (MRI) examination apparatus 32, and an X-ray examination apparatus 34.

The medical image DB server 14 is a so-called picture archiving and communication system (PACS) server that stores and manages the medical image 40 obtained by examination (imaging) using the modality 12.

The clinical terminal 16 and the interpretation terminals 18 are, for example, computers such as personal computers. The clinical terminal 16 is used in a case where a treatment department doctor (or a clinician) 42 who determines the treatment policy of the patient 36 or performs actual treatment creates an electronic medical record, inputs examination reservation information to be described later, and the like. The interpretation terminal 18 is used in a case where a radiologist 44 who interprets the medical image 40 creates a new interpretation report 50 or verifies the already created interpretation report 50.

In addition to the above, the medical information system 10 comprises a hospital information system (HIS) and a radiology information system (RIS).

The HIS receives various kinds of information relevant to medical practices of the medical facility, such as electronic medical records, accounting information, examination reservation information, and medication prescription information, from each department of the medical facility, such as a treatment department and a radiology department, and stores and manages the various kinds of information.

Patient information is registered in the electronic medical record. The patient information has, for example, items of a patient identification (ID) for identifying each patient 36 and the name, sex, date of birth, age, height, and weight of the patient 36. The examination reservation information is input by the treatment department doctor (or the clinician) 42 through the clinical terminal 16.

The examination reservation information includes not only various examination reservations, such as a blood test and an endoscopic examination, but also an imaging order that is an examination reservation using the modality 12. The imaging order is for instructing a user 52 of the modality 12 to perform imaging.

The RIS receives the imaging order input through the clinical terminal 16, and stores and manages the imaging order.

The imaging order has, for example, items of an order ID for identifying each order, a doctor ID of the treatment department doctor (or the clinician) 42 who inputs the imaging order, the type of the modality 12 used in the imaging order, a patient ID of the patient 36 to be imaged, and an imaging part or direction. The imaging part includes not only rough parts in a case where the human body is roughly divided, such as the head, the chest, and the abdomen, but also parts obtained by subdividing the parts. The direction includes supine, prone, recumbent, and the like.

The RIS transmits the imaging order to the modality 12. For example, the user 52 of the modality 12 checks the imaging order on the display of the console of the modality 12, and acquires the medical image 40 by performing imaging under the imaging conditions corresponding to the checked imaging order.

The medical image 40 obtained by imaging is stored in the medical image DB server 14 together with the patient ID of the patient 36 to be imaged (subject), the imaging part or direction, the imaging conditions, imaging date and time, the type of the modality 12 used in the imaging, the ID of the user 52 in charge of imaging, and the like.

In a case where an interpretation request is included in the imaging order, the RIS transmits to the interpretation terminal 18 the order of interpretation of the medical image 40 obtained by imaging. The radiologist 44 checks the order through the interpretation terminal 18, and creates the interpretation report 50 according to the checked order.

The created interpretation report 50 is transmitted to the interpretation DB server 20 and stored therein.

The treatment department doctor (or the clinician) 42 accesses the interpretation DB server 20 from the clinical terminal 16, and determines the treatment policy of the patient 36 or performs the treatment with reference to the interpretation report 50.

Figure 2:
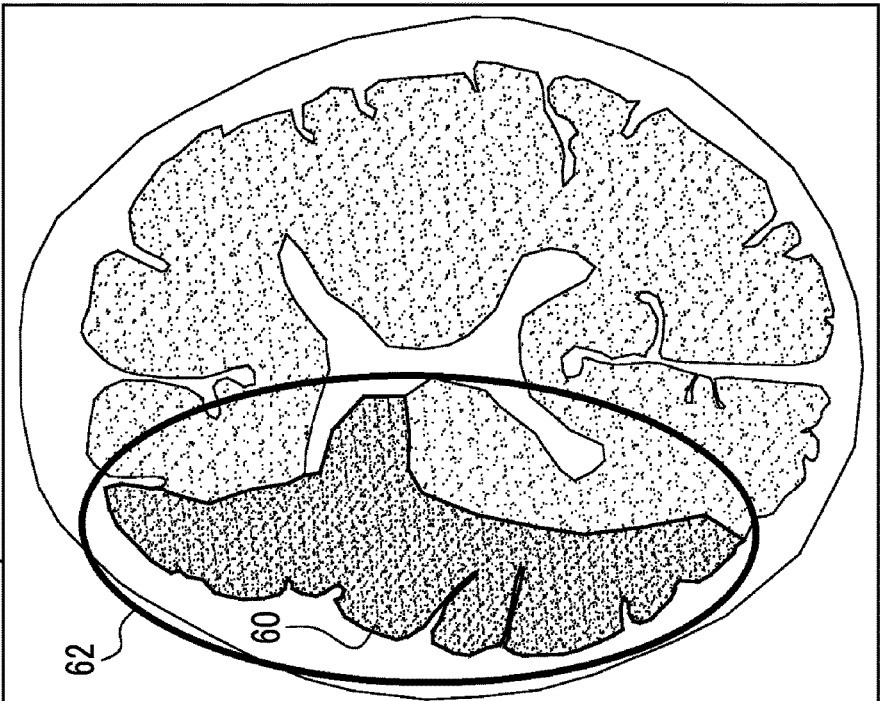
FIG. 2 is an explanatory diagram of an interpretation report.
Figure 3:
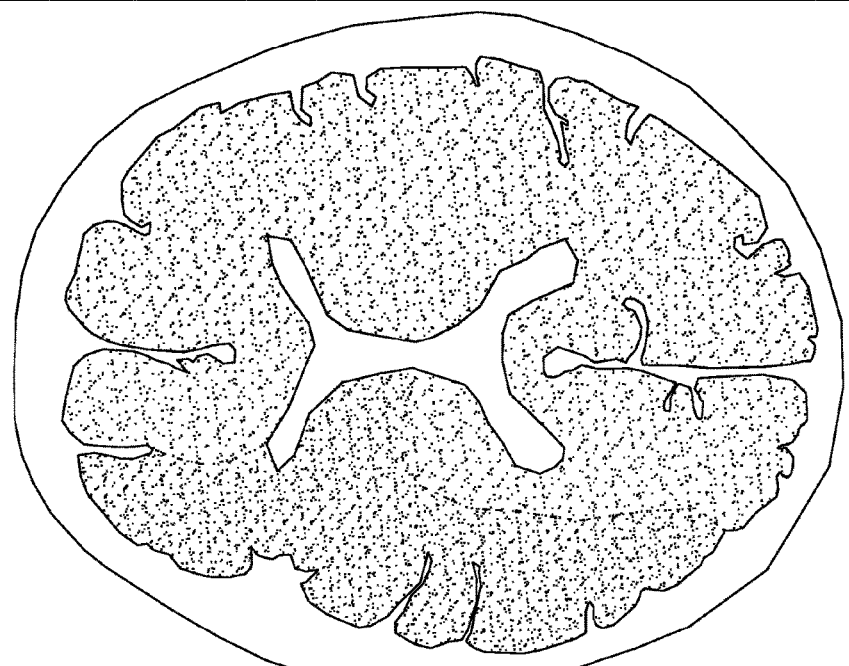
FIG. 3 is an explanatory diagram of an interpretation report.

As shown in FIGS. 2 and 3, in the interpretation report 50, the medical image 40 and various kinds of information regarding the medical image 40 are associated with each other. Various kinds of information regarding the medical image 40 include the type of the modality 12 used for imaging, the name of the patient 36 to be imaged, the patient ID, the imaging part or direction, imaging date and time, and the like. In a case where a region to focus on (region of interest) 60 is present in the medical image 40, an indicator 62 indicating the region of interest 60 and findings 64 of the radiologist 44 regarding the region of interest 60 are included in the various kinds of information regarding the medical image 40 (refer to FIG. 2).

FIG. 2 shows the interpretation report 50 (hereinafter, the interpretation report 50 (MRI)) on the medical image 40 (hereinafter, the medical image 40 (MRI)) obtained by imaging the brain of the patient 36 with the MRI examination apparatus 32, and FIG. 3 shows the interpretation report 50 (hereinafter, the interpretation report 50 (CT)) on the medical image 40 (hereinafter, the medical image 40 (CT)) obtained by imaging the same part (brain) of the same patient 36 (in this example, "Fuji Taro") as in FIG. 2 with the CT examination apparatus 30.

The interpretation report 50 (MRI) and the interpretation report 50 (CT) are created based on an MRI examination and a CT examination performed, for example, as a result of sudden collapse of the patient 36.

Then, in the interpretation report 50 (MRI), a region having a shadow different from other parts can be checked in the medical image 40 (MRI). This region is set as the region of interest 60 and the indicator 62 is given thereto, and a suspicion of cerebral infarction is pointed out in the findings 64 for the region of interest 60.

On the other hand, in the interpretation report 50 (CT), a region having a shadow different from other parts is present in the medical image 40 (CT) as in the medical image 40 (MRI), but it is difficult to check the region compared with the medical image 40 (MRI). Accordingly, the region of interest 60 is not set, and a suspicion of abnormality (cerebral infarction) is not pointed out in the findings 64 either.

As described above, the advantages of the modality 12 are different depending on the type. For example, as in the examples shown in FIGS. 2 and 3, the MRI examination apparatus 32 has an advantage that this is suitable for finding a cerebral infarction. The MRI examination apparatus 32 also has an advantage that there is no radiation exposure.

On the other hand, compared with the MRI examination apparatus 32, the CT examination apparatus 30 has advantages that the examination time is short and accordingly this is suitable for a wide range of examination, but there is also a disadvantage that it is difficult to find a cerebral infarction since the density difference between a lesion portion and a normal portion tends to be poor.

For this reason, the interpretation DB server 20 has an interpretation support function for improving the interpretation technique of the radiologist 44 so that, for example, a cerebral infarction can be found from the medical image 40 (CT) shown in FIG. 3.

Hereinafter, the contents of the interpretation support function and the configuration for realizing the interpretation support function will be described.

Figure 4:
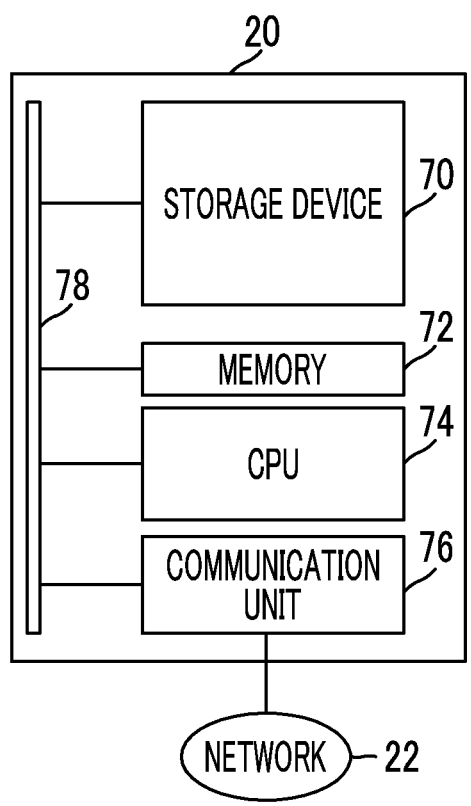
FIG. 4 is a block diagram showing the configuration of an interpretation terminal.

In FIG. 4, the interpretation DB server 20 is a known computer, and comprises a storage device 70 (storage unit), a memory 72, a central processing unit (CPU) 74, and a communication unit 76. These are connected to each other through a data bus 78.

The storage device 70 is a hard disk drive, which is built into a computer that forms the interpretation DB server 20 or the like or which is connected to the computer through a cable or a network, or a disk array formed by connecting a plurality of hard disk drives.

The memory 72 is a work memory for the CPU 74 to execute processing.

The CPU 74 performs overall control of each unit of the computer by loading a program stored in the storage device 70 to the memory 72, thereby executing the processing according to the program.

The communication unit 76 is a network interface to perform transmission control of various kinds of information through the network 22.

Figure 5:
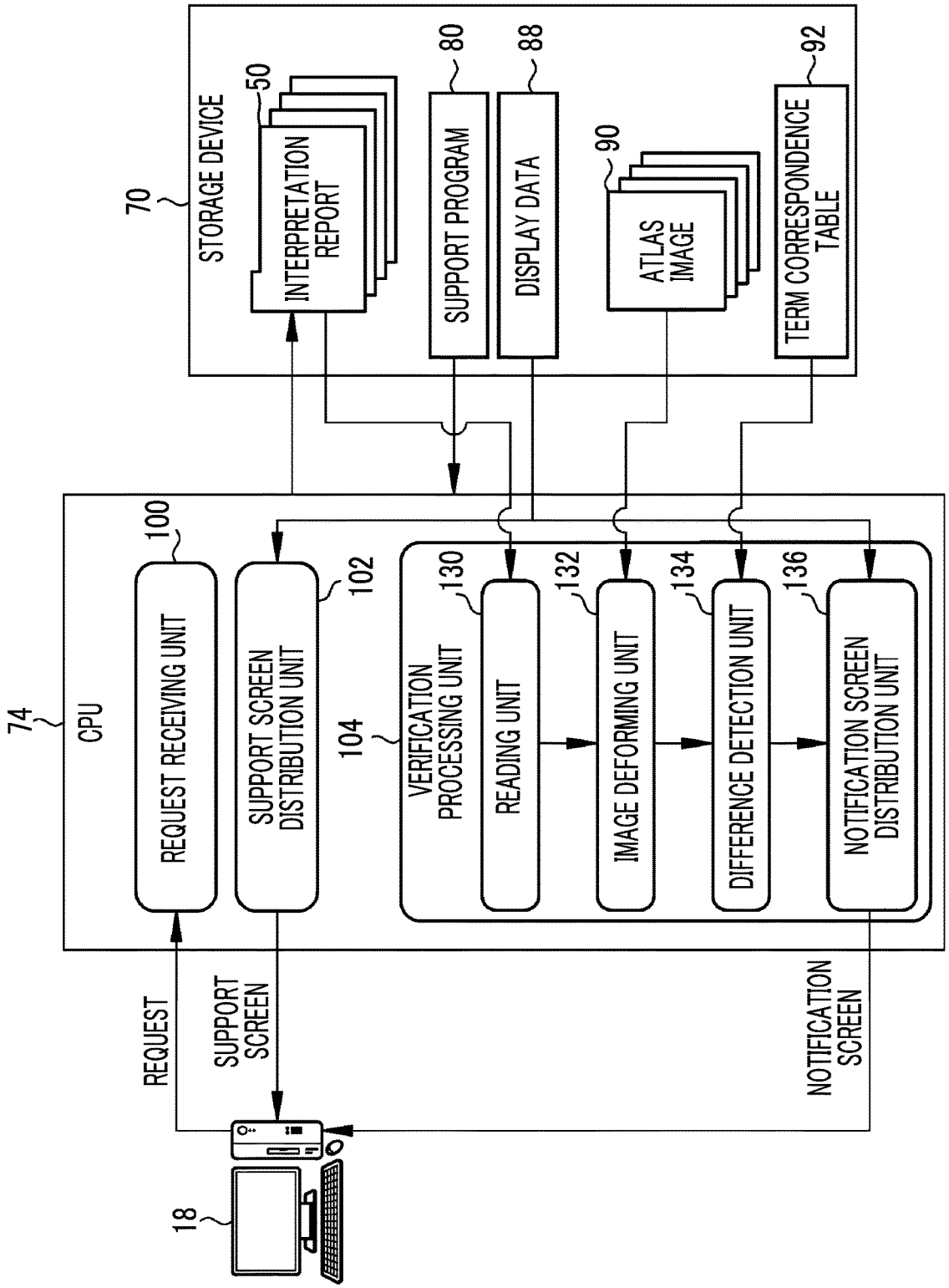
FIG. 5 is an explanatory diagram of each processing unit constructed in an interpretation DB server.

As shown in FIG. 5, in addition to the interpretation report 50 described above, a control program such as an operating system, various application programs, and various kinds of data attached to these programs are stored in the storage device 70.

Specifically, a support program 80 (interpretation support program) is stored as an application program, and display data 88 for displaying support screens 82 and 84 (refer to FIGS. 6 and 7), a notification screen 86 (refer to FIG. 10), and the like an atlas image 90 (refer to FIG. 8), and a term correspondence table 92 (correspondence table) (refer to FIG. 9) are stored as data attached to the support program 80.

The support program 80 is an application program for causing a computer forming the interpretation DB server 20 to function as an interpretation support apparatus having an interpretation support function. The support program 80 is activated by accessing the interpretation DB server 20 from the interpretation terminal 18 and inputting an operation request.

In a case where the support program 80 is activated, the CPU 74 of the interpretation DB server 20 cooperates with the memory 72 or the like to function as a request receiving unit 100, a support screen distribution unit 102, and a verification processing unit 104.

The request receiving unit 100 receives various requests input from the interpretation terminal 18 through the support screens 82 and 84 or the like.

Figure 6:
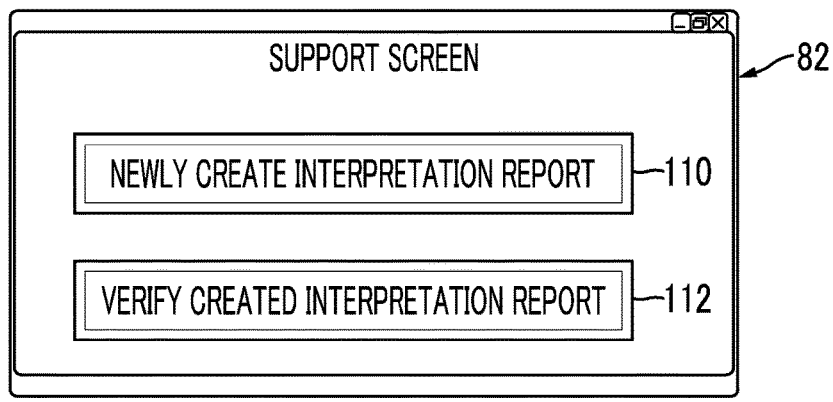
FIG. 6 is an explanatory diagram of a support screen.
Figure 7:
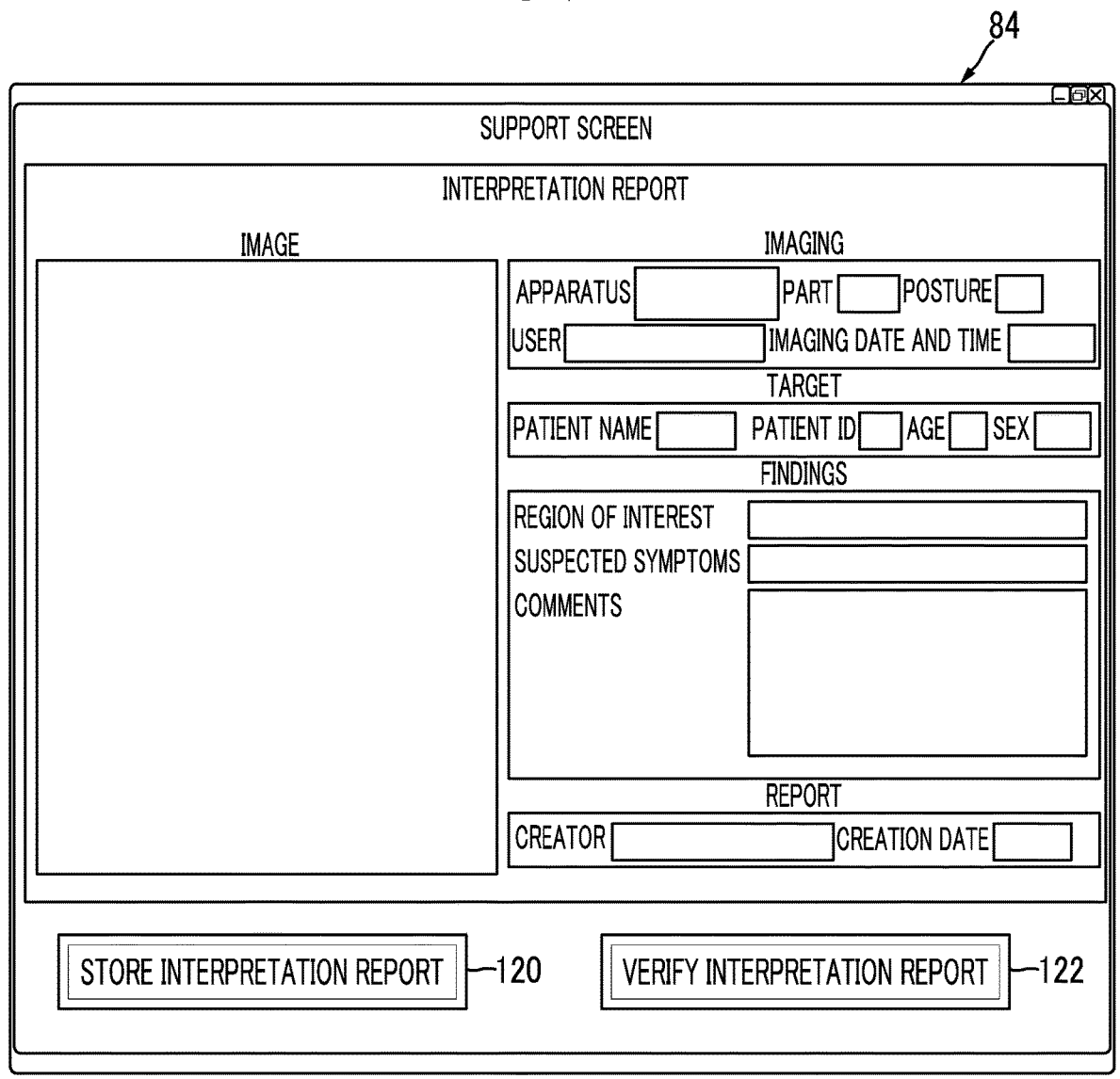
FIG. 7 is an explanatory diagram of a support screen.

The support screen distribution unit 102 distributes the support screen 82 shown in FIG. 6 to the interpretation terminal 18 according to the activation of the support program 80. The distributed support screen 82 is displayed on the display of the interpretation terminal 18. An interpretation report new creation tag 110 and a created interpretation report verification tag 112 are provided on the support screen 82. In the interpretation terminal 18, the interpretation report new creation tag 110 or the created interpretation report verification tag 112 can be selected by an operation such as moving a cursor with a mouse and clicking.

In a case where the interpretation report new creation tag 110 is selected, a new creation support request is input to the support screen distribution unit 102 through the request receiving unit 100. The support screen distribution unit 102 distributes the support screen 84 shown in FIG. 7 to the interpretation terminal 18 according to the input of the new creation support request. The distributed support screen 84 is displayed on the display of the interpretation terminal 18. The support screen 84 has a function as a template in which each item of the interpretation report 50 is blank, and the new interpretation report 50 can be created by inputting information to each item, for example, by operating the interpretation terminal 18 to input characters or pasting the medical image 40. An interpretation report storage tag 120 is provided on the support screen 84, and the interpretation report 50 created through the support screen 84 is stored in the storage device 70 by selecting the interpretation report storage tag 120.

An interpretation report verification tag 122 is provided on the support screen 84. By selecting the interpretation report verification tag 122, the verification processing unit 104 (refer to FIG. 5) operates to perform verification processing on the interpretation report 50 created through the support screen 84. The verification processing is for detecting oversight in the interpretation report 50. As shown in FIG. 5, the verification processing unit 104 functions as a reading unit 130, an image deforming unit 132, a difference detection unit 134, and a notification screen distribution unit 136 (display control unit), and executes verification processing.

In accordance with the start of the verification processing, the reading unit 130 reads the interpretation report 50 in which oversight is to be detected (hereinafter, a detection target interpretation report 50a) and the interpretation report 50 used for comparison with the detection target interpretation report (hereinafter, a comparison target interpretation report 50b).

The detection target interpretation report 50a is the interpretation report 50 newly created through the support screen 84 in a case where the verification processing is started by selecting the interpretation report verification tag 122 of the support screen 84 as described above.

On the other hand, the comparison target interpretation report 50b is the interpretation report 50 created based on the medical image 40 (hereinafter, a comparison target medical image 40b) obtained by imaging the same part of the same patient as in the medical image 40 (hereinafter, a detection target medical image 40a) of the detection target interpretation report 50a, at the same imaging posture. The reading unit 130 searches and reads an interpretation report matching the conditions among the interpretation reports stored in the storage device 70.

Hereinafter, an example will be described in which the detection target interpretation report 50a is the interpretation report 50 (CT) shown in FIG. 3 and the comparison target interpretation report 50b is the interpretation report 50 (MRI) shown in FIG. 2.

In this example, an example in which there is one comparison target interpretation report 50b will be described. However, a plurality of comparison target interpretation report 50b may be used.

In this example, the comparison target interpretation report 50b is created based on the medical image 40 obtained by a different type of modality 12 from the detection target interpretation report 50a. However, the comparison target interpretation report 50b may be created based on the medical image 40 obtained by the same type of modality 12 as the detection target interpretation report 50a.

In addition, in this example, an example will be described in which the detection target interpretation report 50a and the comparison target interpretation report 50b are created based on the medical image 40 obtained by head examination. However, the detection target interpretation report 50a and the comparison target interpretation report 50b may be created based on the medical image 40 obtained by examinations other than the head examination. The detection target interpretation report 50a and the comparison target interpretation report 50b may be created based on the medical image 40 obtained by imaging the same part of the same patient at the same imaging posture.

Figure 8:
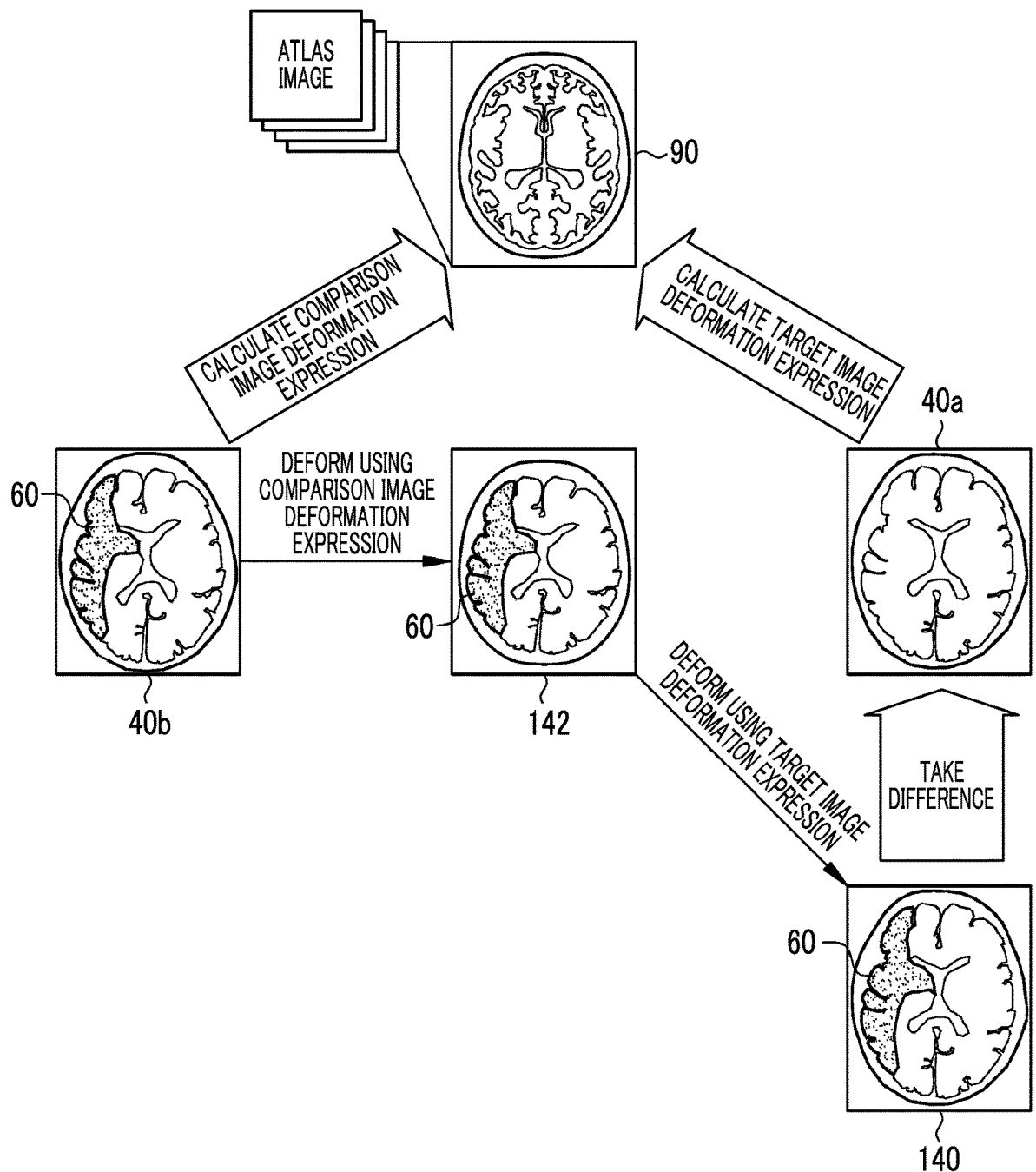
FIG. 8 is an explanatory diagram showing how a comparison target medical image is deformed so that the position of each portion matches a detection target medical image.

As shown in FIG. 8, the image deforming unit 132 extracts the detection target medical image 40a and the comparison target medical image 40b from the detection target interpretation report 50a and the comparison target interpretation report 50b read by the reading unit 130. Then, a deformed image 140 is generated by deforming the comparison target medical image 40b so that the position of each portion of the comparison target medical image 40b matches the position of each portion of the detection target medical image 40a.

Specifically, the image deforming unit 132 accesses the storage device 70 to search and extract an atlas image 90 having the same part (imaging part) and posture (imaging posture) as in the detection target medical image 40a and the comparison target medical image 40b.

The atlas image 90 is an image itself obtained in a case where a standard human body is imaged by the modality 12 or an image created by modeling on such an image, and a plurality of images corresponding to differences in parts or postures are prepared in advance (stored in the storage device 70).

Then, the image deforming unit 132 calculates a deformation expression for deforming the comparison target medical image 40b so that the extracted atlas image 90 and the position of each portion match each other (hereinafter, referred to as a comparison image deformation expression) and a deformation expression for deforming the detection target medical image 40a so that the extracted atlas image 90 and the position of each portion match each other (hereinafter, referred to as a target image deformation expression).

Then, the image deforming unit 132 generates an intermediate image 142 obtained by deforming the comparison target medical image 40b with the comparison image deformation expression so that the position of each portion matches the extracted atlas image 90. In addition, the image deforming unit 132 generates the deformed image 140 by deforming the intermediate image 142 using the target image deformation expression so that the position of each portion matches the detection target medical image 40a.

That is, the image deforming unit 132 generates the deformed image 140 by deforming the comparison target medical image 40b in two stages so that the position of each portion matches the detection target medical image 40a.

Although the example of generating the deformed image 140 by deforming the comparison target medical image 40b in two stages has been described, the deformed image 140 may be generated by one deformation without using (generating) the intermediate image 142 by calculating a deformation expression, which is for generating the deformed image 140 by one deformation from the comparison target medical image 40b, based on the comparison image deformation expression and the target image deformation expression and deforming the comparison target medical image 40b with the calculated deformation expression.

The difference detection unit 134 examines the presence or absence of a region of interest, which is present in the comparison target interpretation report 50b (comparison target medical image 40b) but is not present in the detection target interpretation report 50a (detection target medical image 40a), by taking the difference between the deformed image 140 and the detection target medical image 40a. In a case where such a region of interest is present, the region of interest is detected as a difference region.

In this example, the region of interest 60 is present in the comparison target medical image 40b. For this reason, the region of interest 60 is similarly present in the deformed image 140, but no region of interest is present in the detection target medical image 40a. Therefore, the region of interest 60 is detected as a difference region (refer to FIGS. 8 and 10).

On the other hand, in a case where there is a region of interest common to the detection target interpretation report 50a (detection target medical image 40a) and the comparison target interpretation report 50b (comparison target medical image 40b) (in a case where a common region is set as a region of interest), the difference detection unit 134 compares the findings 64 (the findings 64 of the comparison target interpretation report 50b and the findings 64 of the detection target interpretation report 50a) regarding such a common region of interest with each other.

In the storage device 70, a term correspondence table 92 is stored (refer to FIG. 5). The difference detection unit 134 compares the above-described findings 64 with each other with reference to the term correspondence table 92.

As shown in FIG. 9, in the term correspondence table 92, terms having the same meaning are associated with each other. In the example shown in FIG. 9, terms having the same meaning for the brain region are associated with each other, and terms described in items arranged in the horizontal direction in the diagram are identified as the same terms.

Specifically, for "anterior cerebral artery region" (or "ACA"), even an expression of "frontal lobe" (or "parietal lobe") is identified as the same term. Similarly, for "middle cerebral artery region" (or "MCA"), even an expression of "temporal lobe" (or "frontal lobe" or "parietal lobe") is identified as the same term. In addition, for "posterior cerebral artery region" (or "PCA"), even an expression of "parietal lobe" (or "brainstem") is identified as the same term.

For "frontal lobe", even an expression of any one of "motor area" (or "primary motor area"), "motor association area" (or "premotor area"), "prefrontal area" (or "frontal association area"), or "frontal eye area" is identified as the same term.

In addition, for "motor area" (or "primary motor area"), even an expression of "BA4" is identified as the same term. For "motor association area" (or "premotor area"), even an expression of "BA6" is identified as the same term. For "prefrontal area" (or "frontal association area"), even an expression of any one of "BA9 to BA11" is identified as the same term. For "frontal eye area", even an expression of "BA8" is identified as the same term.

In the example shown in FIG. 9, for a disease state such as a disease name, a plurality of disease states having the same meaning are associated. "Disease state A", "disease state A'", and "disease state A''" are identified as the same terms. Similarly, "disease state B" and "disease state B'" are identified as the same terms.

In the term correspondence table, terms having the same meaning among the terms used in the findings 64 may be associated. Therefore, for terms other than the terms shown in FIG. 9, for example, for parts of a patient other than the brain, a plurality of terms indicating the same part may be associated, or a plurality of terms indicating the degree of similarity for the degree of each disease state may be associated.

The difference detection unit 134 regards the terms associated with each other in the term correspondence table 92 as the same terms by referring to the term correspondence table 92, compares the findings 64 with each other, and detects a portion of the findings 64 of the detection target interpretation report 50a, which is different from the findings 64 of the comparison target interpretation report 50b, as difference findings.

In the comparison between the findings 64, in a case where there is a region of interest common to the detection target interpretation report 50a and the comparison target interpretation report 50b as described above, comparison between the findings 64 for the region of interest is performed. In this example, since there is no region of interest common to the detection target interpretation report 50a and the comparison target interpretation report 50b, comparison between the findings 64 is not performed.

The notification screen distribution unit 136 generates a notification screen 150 (refer to FIG. 10) for providing notification of detection results of a difference region and difference findings by the difference detection unit 134, that is, a verification result (verification processing result) of the detection target interpretation report 50a, and distributes the notification screen 150 to the interpretation terminal 18. The distributed notification screen 150 is displayed on the display of the interpretation terminal 18. Therefore, it is possible to check the result of verification processing.

As shown in FIG. 10, in this example, a difference region is present, and difference findings are not present. Therefore, the notification screen 150 for providing notification of the presence of a difference region, that is, the presence of the region of interest 60 that is present in the comparison target medical image 40b (deformed image 140) but is not present in the detection target medical image 40a. Then, the notification screen 150 is distributed to the interpretation terminal 18, thereby providing notification of the presence of a difference region (in this example, the region of interest 60).

In the example shown in FIG. 10, in order to emphasize the presence of a difference region (region of interest 60), the difference region (region of interest 60) is displayed (overlay-displayed) so as to overlap the detection target medical image 40a. However, a portion other than the difference region, for example, the deformed image 140 itself or a part (for example, a region of interest other than the difference region) of the deformed image 140 other than the difference region may be overlay-displayed.

Undoubtedly, in a case where difference findings are detected by verification processing, notification of the presence of difference findings is provided by the notification screen (notification screen for providing notification of the presence of difference findings is generated and distributed).

For example, as shown in FIG. 11, in a case where the common region of interest 60 is present but a suspicion of "cerebral infarction" is pointed out in the findings 64 in the detection target interpretation report 50a and a suspicion of "cerebral hemorrhage" is pointed out in the findings 64 in the comparison target interpretation report 50b, that is, in a case where difference findings are present, notification of the presence of the difference findings is provided by the notification screen 160.

In the example shown in FIG. 11, in order to emphasize the presence of the difference findings, a portion of the findings 64 of the detection target interpretation report 50a, which is different from the findings 64 of the comparison target interpretation report 50b, is underlined. However, in a case where a suspicion of "disease state A" is pointed out in the findings 64 in the detection target interpretation report 50a and a suspicion of "disease state A'" is pointed out in the findings 64 in the comparison target interpretation report 50b, "disease state A" and "disease state A'" can be regarded as the same meaning by referring to the term correspondence table 92 (refer to FIG. 9). For this reason, the difference is not detected as difference findings.

As described above, also in a case where difference findings are detected, notification of the fact (that the difference findings have been detected) is provided by the notification screen in the same manner as in the case where the difference region is detected. Undoubtedly, in a case where both the difference region and the difference findings are detected, notification of the presence of both the difference region and the difference findings is provided by the notification screen.

Returning to FIG. 6, in a case where the created interpretation report verification tag 112 is selected on the support screen 82, an interpretation report designation screen (not shown) is distributed to the interpretation terminal 18 through the support screen distribution unit 102 and is displayed on the display of the interpretation terminal 18.

The interpretation report designation screen is an operation screen for designating the interpretation report 50 as the detection target interpretation report 50a and the interpretation report 50 as the comparison target interpretation report 50b from the interpretation reports 50 stored in the storage device 70. By operating the interpretation terminal 18, it is possible to designate the interpretation report 50 as the detection target interpretation report 50a and the interpretation report 50 as the comparison target interpretation report 50b.

The interpretation report 50 as the detection target interpretation report 50a is designated, for example, by selecting the interpretation report 50 as the detection target interpretation report 50a from the interpretation reports 50 stored in the storage device 70.

Designation of the interpretation report 50 as the comparison target interpretation report 50b is performed, for example, by extracting the interpretation reports 50, which are created based on the medical image 40 obtained by imaging the same part of the same patient as in the interpretation report 50 designated as the detection target interpretation report 50a, from the storage device 70 and selecting the interpretation report 50 as the comparison target interpretation report 50b from the extracted interpretation reports 50.

Then, in a case where the interpretation report 50 as the detection target interpretation report 50a and the interpretation report 50 as the comparison target interpretation report 50b are designated, verification processing is performed in the same manner as in the case where the interpretation report verification tag 122 is selected on the support screen 84 (refer to FIG. 7), and a notification screen (for example, the notification screen 150 shown in FIG. 10 or the notification screen 160 shown in FIG. 11) indicating the verification result is distributed to the interpretation terminal 18.

As described above, in the invention, in a case where a difference region, that is, a region of interest that is present in the comparison target medical image but is not present in the detection target medical image, is detected by performing verification processing, notification of the fact is provided. Therefore, for example, by finding an overlooked lesion by the verification processing, it is possible to contribute to the improvement of the interpretation technique of the radiologist.

Since the detected difference region is overlay-displayed on the detection target medical image, it is easy to understand the difference region at a glance.

In addition, since the detection or overlay display of the difference region is performed after deforming the comparison target medical image so that each part matches the detection target medical image, more appropriate detection or overlay display of the difference region becomes possible.

In a case where a region of interest common to the detection target medical image and the comparison target medical image is set, in a case where there is a difference as a result of comparing the findings on the common region of interest, notification of the fact is provided. This can contribute to the improvement of the interpretation technique more reliably.

In the comparison of findings, since terms having the same meaning are regarded as the same terms by the term correspondence table even in a case where the terms are differently expressed, more accurate comparison is possible.

In addition, since the interpretation report as a detection target interpretation report may be not only a new interpretation report, which is newly created, but also an interpretation report created in the past, it is possible to verify not only the new interpretation report but also the past interpretation report. That is, by reviewing the past interpretation report to check oversight and the like, it is possible to improve the interpretation technique.

In the invention, since verification is performed with one of interpretation reports, which are created based on medical images acquired by examinations using different examination apparatuses, as a detection target interpretation report and the others as comparison target interpretation reports, a noticeable effect can be obtained. In particular, it is effective to verify interpretation reports created based on medical images acquired by examination apparatuses having different characteristics (advantages and disadvantages), such as a CT examination apparatus and an MRI examination apparatus. In addition, it is effective to verify an interpretation report created by an examination in which the result of interpretation has a serious influence on the patient, such as a head examination.

EXPLANATION OF REFERENCES

10: medical information system
12: modality
14: medical image DB server
16: clinical terminal
18: interpretation terminal
20: interpretation DB server (interpretation support apparatus)
22: network
30: CT examination apparatus
32: MRI examination apparatus
34: X-ray examination apparatus
36: patient
40: medical image
42: treatment department doctor (or clinician)

44: radiologist
50: interpretation report
52: user
60: region of interest
62: indicator
64: findings
70: storage device (storage unit)
72: memory
74: CPU
76: communication unit
78: data bus
80: support program (interpretation support program)
82, 84: support screen
86: notification screen
88: display data
90: atlas image
92: term correspondence table (correspondence table)
100: request receiving unit
102: support screen distribution unit
104: verification processing unit
110: interpretation report new creation tag
112: created interpretation report verification tag
120: interpretation report storage tag
122: interpretation report verification tag
130: reading unit
132: image deforming unit
134: difference detection unit
136: notification screen distribution unit (display control unit)
140: deformed image
142: intermediate image
150, 160: notification screen

What is claimed is:

1. An interpretation support apparatus that supports creation of an interpretation report including a medical image obtained by examining a patient, a region of interest to focus on in the medical image, and findings on the region of interest, the apparatus comprising:
a processor configured to:
read a plurality of interpretation reports created by a plurality of examinations on the same part of the same patient;
set one of the plurality of interpretation reports as a detection target interpretation report and set the others as comparison target interpretation reports to be used for comparison with the detection target interpretation report, compare regions of interest of the detection target interpretation report and the comparison target interpretation reports, and detect a region of interest, which is present in the comparison target interpretation reports but is not present in the detection target interpretation report, as a difference region; and
in a case where the difference region is detected by the detection unit, notify that the difference region has been detected;
wherein the processor is further configured to:
deform a comparison target medical image, which is a medical image of the comparison target interpretation report, such that a position of each portion matches a position of each portion of a detection target medical image, which is a medical image of the detection target interpretation report; and
perform overlay display for displaying a region of interest of a deformed comparison target medical image, which is deformed, on a display so as to overlap the detection target medical image.

2. The interpretation support apparatus according to claim 1,
wherein, in a case where the difference region is not present, for a common region of interest that is a region of interest common to both the detection target interpretation report and the comparison target interpretation reports, the processor is further configured to compare findings of the detection target interpretation report and findings of the comparison target interpretation reports regarding the common region of interest with each other and detect, as difference findings, findings not matching the findings of the comparison target interpretation reports in the findings of the detection target interpretation report, and
in a case where the difference findings are detected, the processor is further configured to notify that the difference findings have been detected.

3. The interpretation support apparatus according to claim 2, further comprising:
a storage that stores a correspondence table in which terms having the same meaning are associated with each other for terms used in the findings,
wherein the processor is further configured to detect the difference findings by accessing the storage to refer to the correspondence table.

4. The interpretation support apparatus according to claim 3,
wherein, in the correspondence table, a plurality of terms indicating each part are associated with each other for each part of the patient.

5. The interpretation support apparatus according to claim 1,
wherein the processor is further configured to perform the overlay display for the difference region.

6. The interpretation support apparatus according to claim 1,
wherein the detection target interpretation report and the comparison target interpretation report are created based on examinations using the same examination apparatus.

7. The interpretation support apparatus according to claim 1,
wherein the detection target interpretation report and the comparison target interpretation report are created based on examinations using different examination apparatuses.

8. The interpretation support apparatus according to claim 7,
wherein one of the detection target interpretation report or the comparison target interpretation report is created based on an examination using a magnetic resonance imaging (MRI) examination apparatus, and
the other one of the detection target interpretation report and the comparison target interpretation report is created based on an examination using a computed tomography (CT) examination apparatus.

9. The interpretation support apparatus according to claim 7,
wherein the examination is a head examination,
the detection target interpretation report is created based on an examination using a computed tomography (CT) examination apparatus, and
the comparison target interpretation report is created based on an examination using a magnetic resonance imaging (MM) examination apparatus.

10. A non-transitory computer readable medium for storing a computer-executable program for supporting creation of an interpretation report including a medical image obtained by examining a patient, a region of interest to focus on in the medical image, and findings on the region of interest, the computer-executable program causing the computer to:
  read a plurality of interpretation reports created by a plurality of examinations on the same part of the same patient;
  set one of the plurality of interpretation reports as a detection target interpretation report and set the others as comparison target interpretation reports to be used for comparison with the detection target interpretation report, compare regions of interest of the detection target interpretation report and the comparison target interpretation reports, and detect a region of interest, which is present in the comparison target interpretation reports but is not present in the detection target interpretation report, as a difference region; and
  notify that the difference region has been detected, in a case where the difference region is detected;
  the computer-executable program further causing the computer to:
  deform a comparison target medical image, which is a medical image of the comparison target interpretation report, such that a position of each portion matches a position of each portion of a detection target medical image, which is a medical image of the detection target interpretation report; and
  perform overlay display for displaying a region of interest of a deformed comparison target medical image, which is deformed, on a display so as to overlap the detection target medical image.

* * * * *